(12) United States Patent
Evrard et al.

(10) Patent No.: US 8,886,448 B2
(45) Date of Patent: Nov. 11, 2014

(54) METHOD OF PROVIDING A VOLUME-MASS LAW FOR FUEL CONSUMPTION

(71) Applicant: Airbus Helicopters, Cedex (FR)

(72) Inventors: Jean-Philippe Evrard, Marseille (FR); Cyril Passemard, Salon de Provence (FR)

(73) Assignee: Airbus Helicopters, Marignane Cedex (FR)

( * ) Notice: Subject to any disclaimer, the term of this patent is extended or adjusted under 35 U.S.C. 154(b) by 235 days.

(21) Appl. No.: 13/760,425

(22) Filed: Feb. 6, 2013

(65) Prior Publication Data
US 2013/0211703 A1 Aug. 15, 2013

(30) Foreign Application Priority Data

Feb. 9, 2012 (EP) .................................... 12290047

(51) Int. Cl.
*G06F 19/00* (2011.01)
*G06G 7/70* (2006.01)
*G06G 7/76* (2006.01)
*G01N 33/28* (2006.01)
*G01F 9/00* (2006.01)
*G01F 1/90* (2006.01)
*G06F 17/00* (2006.01)

(52) U.S. Cl.
CPC ............ *G06F 17/00* (2013.01); *G01N 33/2829* (2013.01); *G01F 9/008* (2013.01); *G01F 1/90* (2013.01)
USPC ............................. 701/123; 701/99; 701/100

(58) Field of Classification Search
USPC ............... 701/99, 100, 123; 60/734, 735, 772
See application file for complete search history.

(56) References Cited

U.S. PATENT DOCUMENTS

| | | | |
|---|---|---|---|
| 6,335,690 B1 * | 1/2002 | Konchin et al. | 340/618 |
| 2007/0240506 A1 * | 10/2007 | Lin | 73/304 R |
| 2011/0162448 A1 | 7/2011 | McGaughey | |
| 2012/0042657 A1 | 2/2012 | Hodinot | |

FOREIGN PATENT DOCUMENTS

| | | | |
|---|---|---|---|
| FR | 2945075 A1 | 11/2010 | |
| GB | 828730 A | 2/1960 | |
| WO | 2011084940 A2 | 7/2011 | |

OTHER PUBLICATIONS

Search Report and Written Opinion; EP 12290047; dated Jul. 24, 2012.

* cited by examiner

*Primary Examiner* — Rami Khatib
(74) *Attorney, Agent, or Firm* — Brooks Kushman P.C.

(57) ABSTRACT

A method of providing a volume-mass law for determination of a fuel flow rate of an engine, particularly providing a fuel flow rate to a helicopter turbine, comprising the steps of: determining a sample type of fuel and a start density $\rho_o$ of said sample type of fuel in said fuel tank using an equation $\rho_0 = aT + b_0$, with a and $b_0$ being known for said sample type of fuel and calculating real time offset parameters $b_n$ from an algorithm to determine real time densities $\rho$ of the fuel.

8 Claims, 1 Drawing Sheet

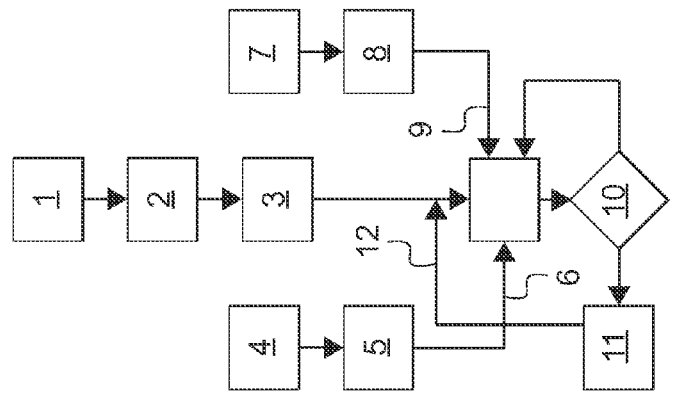
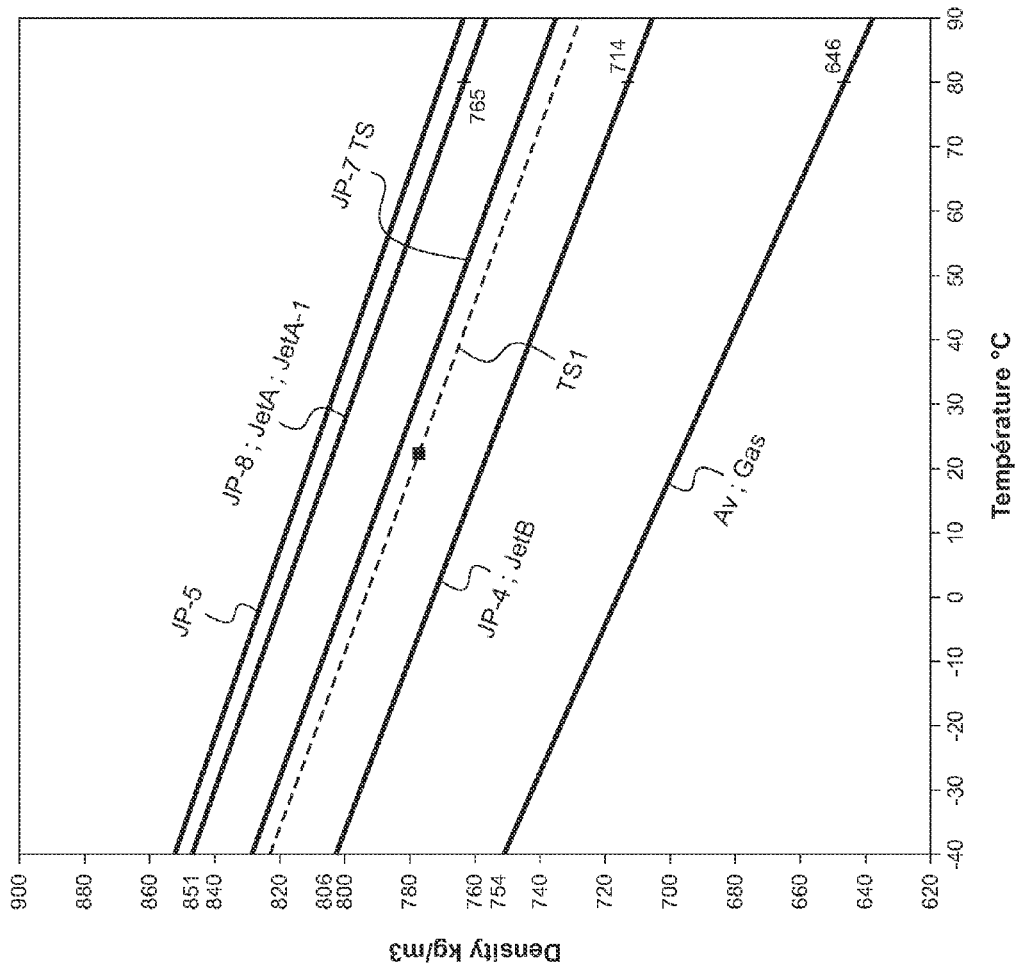

METHOD OF PROVIDING A VOLUME-MASS LAW FOR FUEL CONSUMPTION

CROSS REFERENCE TO RELATED APPLICATIONS

This application claims priority to European application No. 12 290047.5, filed Feb. 9, 2012, the disclosure of which is incorporated in its entirety by reference herein.

BACKGROUND OF THE INVENTION (1) Field of the Invention

The invention is related to a method of providing an accurate volume-mass law for detection of precise fuel consumption of an engine, particularly providing an accurate volume-mass law for detection of precise fuel consumption of a helicopter engine.

(2) Description of Related Art

It is important for any aircraft crew to know precisely how much flight time is still available or to be able to determine how far it is possible to go and at which point it is compulsory to turn around in order to be able to return the take-off area. Long flights with flight sections without landing options, such as flights across the sea, above the jungle, desert or any other hostile areas make it compulsory for the crew of any aircraft to figure out exactly the mass of fuel necessary for an optimization of the mass to be lifted by the aircraft at take-off. With reduced allowances relative to the assessment of quantities while taking into account the different conditions the aircraft might encounter during its flight, e.g. direction and speed of the wind, precise metering means for the flow rate of the mass are necessary for an assessment of the remaining fuel quantity till landing and for the definition of a point of non-return.

The document GB828730 discloses the measure the rate of flow of fuel from the fuel tanks in an aircraft, in terms of mass rather than in terms of volume, for a better indication of the rate at which energy is being used since mass is not effected by changes in the ambient temperature. The flow rate is measured in gravimetric units with a moving coil meter of the dynamometric type, for measuring the volume rate of flow. A current is then passed in fixed coils to obtain results proportional to the density of the fluid. This involves integration of specific devices for metering the flow rate.

The document WO2011084940 discloses a sensor element in a fuel system, and in particular, to a potential electro-static differential level sensor element for measuring fuel levels and fuel type in a fuel system. A sensor element includes two electrode plates mounted on a dielectric material and secured to a shield plate. The sensor element is extruded to form a three dimensional sensor element, such as a spiral coil, that has increased capacitance detection ability to measure fuel type and level.

The document FR2945075 discloses a controlled high-pressure fuel flow which is fed into a combustion chamber via a valve, the position of which is controlled, and a shut-off and pressurization check valve with variable opening. A value representing the actual mass flow of fuel supplied is calculated by a computation unit from information representing the pressure difference between the input and output of the check valve and the clearance through the check valve, for example, resulting in the position X of the check valve slide. The valve has a variable position controlled by the computation unit according to the difference between the calculated value representing the actual mass flow and a value representing a desired mass flow. A sensor element recognizes the permittivity and from the permittivity the type of fuel in the system.

BRIEF SUMMARY OF THE INVENTION

Up to date there are metering devices for the flow rate in a fuel system of a helicopter such as 1) flow metering devices of the turbine type mounted in series with the fuel supply line upstream of the engine are delicate with regard to constipation (i.e. obstruction) in case of freezing conditions or in case of polluted fuel, 2) flow metering devices of the turbine type mounted in series with the fuel supply line downstream of the fuel heating unite and consequently not delicate with regard to freezing as the fuel is heated before reaching the flow metering device, 3) devices exclusively based on the opening of a dosing feeder of the engine, said dosing feeder being used to regulate the engine and consequently having a fairly good level of precision thus allowing knowledge of the real time volume flow rate.

There are a certain number of disadvantages related to these metering devices:

1) An increase of pressure losses along the fuel supply line at normal operation and in freezing conditions, increased risks of constipation of the turbine type flow metering device and necessity to take into account this type of failure for any pressure losses of the fuel supply line. There is no possibility to mount the turbine type flow metering device to a suction type system, i.e. to a system with an engine able to aspirate the fuel from a fuel tank without any need for one or several pumps mounted between said fuel tank and the engine. From that follows the need for specific equipment, such as a turbine type flow metering device, to meter the flow rate with consequences as to mass and costs increase, and overall system reliability decrease.

2) An increase of pressure losses along the fuel supply line at normal operation, increased risks of constipation of the turbine type flow metering device and necessity to take into account this type of failure for any pressure losses of the fuel supply line. There is the need for a specific equipment to meter the flow rate with consequences as to mass and costs increase and overall system reliability decrease.

3) Bad precision for the measure of the mass flow rate from the only information "degree of opening of the dosing feeder", the bad precision being basically due to the conversion of the fairly accurate volume flow rate to the mass flow rate not being up to the expectations regarding precision of the flying staff. The conversion is indeed established on the base of a relation for a volume-mass dependent from the temperature. This relation varies significantly for the different types of fuel customarily used with helicopter turbines, such as Jet A1, JP-4, RT-1, etc. and within one and the same type of fuel depending from the composition and/or the pollution of the actually used fuel.

It is an object of the invention to provide an accurate volume-mass law for a determination of precise fuel flow rates of an engine to operators such as a pilot crew of a helicopter.

An object of the invention is a method of providing an accurate volume-mass law for a determination of precise fuel flow rates of an engine with the features of claim 1.

According to an embodiment of the invention a method of providing an accurate volume-mass law for determination of precise fuel flow rates from a fuel tank to an engine, particularly a method of providing an accurate volume-mass law for determination of precise fuel flow rates from the fuel tank to a helicopter turbine, to allow calculation of remaining flight time, point of non-return and fuel quantity left in the fuel tank till landing, comprises the steps of: Measuring a permittivity ξ of fuel in the fuel tank of the engine and measuring a temperature $T_R$ of fuel in said fuel tank. A sample type of fuel with a given density $\rho_0$ in said fuel tank is detected by associating the measured permittivity ξ and temperature $T_R$ of the fuel in said fuel tank to at least one corresponding data pair ξ, T, stored in a memory and selected from different types of known fuels. Temperatures Tm and instant flow rates of the sample type of fuel are detected at defined times $t_n$, $t_{n-1}$ ... at a dosing feeder of the engine and either fuel volumes and temperatures $T_R$ or fuel masses are provided at defined times $t_n$, $t_{n-1}$ ... in said fuel tank. Accurate real-time parameters a, b of equations $\rho=aT+b$ for real-time densities $\rho_n$, $\rho_{n-1}$ ... at defined times $t_n$, $t_{-1}$ ... are calculated from either the fuel volumes and the temperature $T_R$ or fuel masses at defined times $t_n$, $t_{n-1}$ ... in said fuel tank and from said instant flow rates from said engine integrated with $\Delta t = t_n - t_{n-1}$ the temperature Tm for the accurate volume-mass law of the sample type of fuel. The time intervals $\Delta t$ are about 1 min. between consecutive calculations for the respective densities $\rho_n$, $\rho_{n-1}$ ... The inventive method allows an establishment of an accurate volume-mass law without installation of any supplemental metering devices but enabling an enhanced conversion from volume flow rate to mass flow rate for the sample type of fuel. Said accurate volume-mass law may be used for a determination of precise fuel flow rates of an engine. Said precise fuel flow rates to an engine may be communicated to operators, such as a pilot crew of a helicopter for an assessment of the remaining fuel quantity till landing and for the definition of a point of non-return.

According to an embodiment of the invention, e.g. for determination of a fuel flow rate to a helicopter turbine, comprises the steps of: Determining a start density ρo of said sample type of fuel in said fuel tank using an equation $\rho_0=aT+b_0$, with a and $b_0$ being known parameters for said sample type of fuel. The respective masses $M_{Rn}$, $M_{Rn-1}$ of fuel are given by the fuel system at times $t_n$, $t_{n-1}$ ... in said fuel tank and respective fuel mass difference $\Delta M_{Rn}$, $\Delta M_{Rn-1}$ of fuel at times $t_n$, $t_{n-1}$ are calculated, providing the mass of fuel consumed in said fuel tank within time intervals $\Delta t$ between times $t_n$, $t_{n-1}$ ... for operation of the engine at a medium (i.e. average) temperature $T_R$, said medium temperature $T_R$ being calculated during the time intervals $t_{n-1}$ till $t_n$ ... in the fuel tank. A volume flow of fuel Qm is continuously measured across a dosing feeder of the operating engine and the temperature Tm is measured at said dosing feeder of the operating engine. The volume flow of fuel Qm is integrated during the time intervals $t_{n-1}$ till $t_n$ ... of operation to the volume of fuel consumption Vm of the engine at a medium temperature Tm, said medium temperature Tm being calculated during the time interval $t_{n-1}$ till $t_n$ ... A dosing meter mass $\Delta Mm_n$ is calculated from the consumed volume Vm of fuel at said dosing feeder by using the equation $\rho=aT+b_n$ and the fuel tank mass $\Delta M_{Rn}$ is balanced with the dosing meter mass $Mm_n$. A correction factor $K_x$ is provided for calculation of a new offset $b_n=K_x \times b_{n-1}$ if the balance of the fuel tank mass $\Delta M_{Rn}$ with the dosing meter mass $\Delta Mm_n$ is different from 0. Said new offset $b_n$ is applied to the equation $\rho=aT+b_n$ before the next respective calculation of fuel tank mass Mr and the dosing meter mass Mm by using the equation $\rho=aT+b_n$.

Said new offset parameter $b_n$ is applied to the equation $\rho_n=aT+b_n$ before the respective calculation of fuel density $\rho_n$ at $t_n$. Said respective calculations of fuel density at ... $t_{n-1}$, $t_n$ are repeated as many times as needed till landing to calculate x real time subsequent new offset parameters $b_x$, for subsequent time intervals $\Delta t$. The invention allows—after automatic recognition of the fuel type on board—and immediately after start of the method a continuously more precise definition for real time densities of fuel consumed during operation of an engine with an increased precision of the intended flow rate. With an amount of fuel indicated by the fuel system the inventive method allows for a helicopter a precise forecast of remaining flight time and a definition of a point of non-return is possible. The advantages of the inventive method and its embodiments can be accomplished at the cost of some extra load to the central processing units of the engine but without any further costs as there is no need for any specific flow rate metering equipment. The inventive method can be applied without supplemental weight, as there is no need for any specific flow rate metering equipment. The inventive method allows an increased safety and reliability, as there is no need for any specific flow rate metering equipment and the inventive method allows an optimized sizing of the fuel system due to the lack of devices causing pressure losses in the supply line, particularly in case of ice and pollution. The inventive method allows improved precision for the flow rate without integration of specific devices for metering the flow rate compared to existing systems.

According to a further embodiment, are provided for the case that the respective masses $M_{Rn}$, $M_{Rn-1}$ of fuel are not given by the avionic system at times $t_n$, $t_{n-1}$ ... in said fuel tank. Said embodiment comprises the steps of: Determining a start density ρo of said sample type of fuel in said fuel tank using an equation $\rho_0=aT+b_0$, with a and $b_0$ being known for said sample type of fuel, measuring a volume $V_{Rn}$ of fuel at a time $t_n$ in said fuel tank, measuring a volume $V_{Rn-1}$ of fuel at a time $t_{n-1}$ in said fuel tank and calculating from the volume $V_{Rn}$ and the volume $V_{Rn-1}$ a fuel volume difference $\Delta V_{Rn}$ at a time $t_n$ for the fuel consumed in said fuel tank within said time interval $\Delta t$, for operation of the engine. A medium temperature $T_R$ is metered and calculated during the time interval $t_{n-1}$ till $t_n$ in the fuel tank. A volume flow of fuel Qm across a dosing feeder of the operating engine is measured at a time $t_n$ and the temperature Tm at said dosing feeder of the operating engine. The volume flow of fuel Qm is integrated during the time interval $t_{n-1}$ till $t_n$ of operation to the fuel consumption Vm of the engine and a medium temperature Tm during the time interval $t_{n-1}$ till $t_n$ is calculated. For the time $t_n$ a real time offset parameter $b_n$ is calculated from an algorithm using the temperature Tm at said dosing feeder, the consumed volume Vm of fuel at said dosing feeder during the time interval $t_{n-1}$ till $t_n$ and a mass $\Delta M_{Rn}$ of fuel consumed in said fuel tank during the time interval $t_{n-1}$ till $t_n$ by using the fuel volume difference $\Delta V_{Rn}$. Said new offset parameter $b_n$ is applied to the equation $\rho=aT+b_n$ before the respective calculation of fuel density $\rho_n$ at $t_n$. The steps b-j) are repeated x times to calculate x subsequent new offset parameters $b_x$ for subsequent time intervals $\Delta t_x$.

According to a further embodiment, for the case that the respective masses $M_{Rn}$, $M_{Rn-1}$ of fuel are not given by the avionic system at times $t_n$, $t_{n-1}$ ... in said fuel tank, the real time offset parameter $b_n$ at a time $t_n$ is calculated from an algorithm:

$$b_n = \frac{a\left[T_m \times \int_{t_{n-1}}^{t_n} Q_m dt - T_R(V_{Rn} - V_{Rn-1})\right]}{(V_{Rn} - V_{Rn-1}) - \int_{t_{n-1}}^{t_n} Q_m dt}$$

with $T_R$ being the mean temperature of the fuel tank indicated by the fuel system calculated during the time interval $t_{n-1}$ till $t_n$, Tm being the mean fuel temperature at the dosing feeder indicated by the Full Authority Digital Engine Control (FADEC) calculated during the time interval $t_{n-1}$ till $t_n$, $V_R$ being the volume of the fuel tank indicated by the calibration means of the system corrected according to the attitude of the vehicle and Qm being the volume flow rate of the fuel at the dosing feeder indicated by the FADEC.

According to a further preferred embodiment of the invention for the case that the respective masses $M_{Rn}$, $M_{Rn-1}$ of fuel are not given by the fuel system at times $t_n$, $t_{n-1}$ ... in said fuel tank, the volume Vm of fuel consumed is calculated by integrating the volume flow of fuel Qm during the time interval $\Delta t_n$ of operation of the engine at the medium temperature Tm, calculating a fuel tank mass $M_R$ from the consumed volume $V_{Rn}$ of fuel in said fuel tank by using the equation $\rho_n = aT + b_n$, calculating a dosing meter mass Mm from the consumed volume Vm of fuel at said dosing feeder by using the equation $\rho_n = aT + b_n$, balancing the fuel tank mass $M_R$ with the dosing meter mass Mm, providing a correction factor $K_n$ and calculating a new offset $b_{n+1} = K_n \times b_n$ if the balance of the fuel tank mass $M_R$ with the dosing meter mass Mm is different from 0 and applying said new offset $b_{n+1}$ to the equation $\rho_n = aT + b_n$ before the next respective calculation of fuel tank mass $M_R$ with the dosing meter mass Mm by using the equation $\rho_{n+1} = aT + b_{n+1}$.

According to a further embodiment a refined parameter "a" of the equation $\rho = aT + b_n$ is calculated from an algorithm:

$$a = f(\text{permittivity and temperature of the fuel}) \text{ indicated by the fuel system.}$$

The refined parameter "a" allows a more precise determination of real time densities $\rho$ of fuel consumed during operation of an engine.

According to a further preferred embodiment the results of the algorithms are displayed to the crew operating the engine.

According to a further preferred embodiment further parameters of the helicopter are metered, e.g. speed, present position, coordinates of the landing.

BRIEF DESCRIPTION OF THE SEVERAL VIEWS OF THE DRAWINGS

The following description is made with reference to the attached drawings.

FIG. 1 shows a chart with densities for different types of fuel used for the invention; and FIG. 2 shows a flow chart of a method for establishing an accurate volume-mass law for determination of a fuel flow rate to a helicopter turbine for determining a fuel flow rate according to the invention.

DETAILED DESCRIPTION OF THE INVENTION

According to FIG. 1 different types of fuel customarily used with helicopter turbines, such as JP-5, JP-8, JET A, Jet A-1, JP-7, TS, JP-4, JET B and Av. Gas are presented with their respective densities as quasi linear functions of temperature that can be described with an algorithm $\rho_0 = aT + b_0$ with a being the gradient and $b_0$ representing the offset parameter for the sample fuel. The data of said different types of fuel are stored and accessible in an on board memory.

The gradients defined by the value of parameter "a" of said quasi linear functions are basically the same. The respective offset parameters $b_0$ of said quasi linear functions represent the main differences between the different types of fuel.

According to FIG. 2 a step 1 of a method of establishing an accurate volume-mass law for determination of a fuel flow rate to a helicopter turbine for measuring a fuel flow rate to this turbine (not shown) comprises metering the permittivity $\xi$ and the temperature $T_R$ of the fuel in a fuel tank by means of the fuel system in an avionic system of the helicopter.

The permittivity $\xi$ and the temperature $T_R$ of the fuel in a fuel tank are provided to an avionic system for determination in a step 2 of the sample fuel type from a fuel type data pool. With the type of sample fuel an equation for the density is determined in a step 3 according to the algorithm $\rho_0 = aT + b_0$.

In a step 4 of the method of measuring the fuel flow rate the volume $V_{Rn}$ and the temperature $T_R$ of the fuel in the fuel tank are measured at a time $t_n$ by means of the fuel system and said data are provided to the avionic system. In a step 5 in the avionic system the consumed fuel volume is calculated from the fuel volume $V_{Rn-1}$ at a time $t_{n-1}$ and the volume $V_{Rn}$ of fuel at a time $t_n$. The medium temperature $T_R$ during the time interval $t_{n-1}$ till $t_n$ of the fuel in the fuel tank is determined in the avionic system. In a step 6 the mass Mr of the consumed fuel volume from the fuel tank at the medium temperature $T_R$ is calculated in the avionic system by means of the algorithm $\rho_{n-1} = aT + b_{n-1}$.

In a step 7 a "Full Authority Digital Engine Control" (FADEC, not shown) meters the volume flow rate of fuel Qm and the temperature Tm at said dosing feeder of the helicopter's turbine as operating engine and said data are provided to the avionic system. The temperature Tm is metered at said dosing feeder or alternative upstream of said dosing feeder. The temperature Tm is corrected according to a law known in the field of engines and is calibrated on a test bench to find out the temperature Tm at said dosing feeder. In a step 8 the avionic system integrates the volume flow of fuel Qm during the time interval $\Delta t$ from $t_{n-1}$ till $t_n$ of operation to the fuel consumption Vm of the engine at a medium temperature Tm during the time interval $t_{n-1}$ till $t_n$ at a dosing feeder. The time intervals $\Delta t$ are about 1 min.

The mass Mm of the consumed fuel volume at the dosing feeder at the medium temperature Tm is calculated in the avionic system in a step 9 by means of the algorithm $\rho_{n-1} = aT + b_{n-1}$.

In a step 10 the mass Mr calculated from the consumed fuel volume from the fuel tank is compared with the mass Mm calculated from the consumed fuel volume at the dosing feeder. If the difference between the mass Mr and the mass Mm is different from zero a correction factor k is calculated in a step 11 to provide a new offset parameter $b_n$ with the equation: $b_n = k \times b_{n-1}$. Before the next calculations of mass Mr from the consumed fuel volume from the fuel tank and the mass Mm calculated from the consumed fuel volume at the dosing feeder instead of the offset parameter $b_n - 1$ the new offset parameter $b_n$ is used in the algorithm $\rho_n = aT + b_n$ in a step 12 for a more precise calculation of the next real time density $\rho_n$ of the fuel and the subsequently resulting mass Mr from the consumed fuel volume from the fuel tank and the mass Mm calculated from the consumed fuel volume at the dosing feeder.

The more precise calculations of the real time densities $\rho_n$ of the fuel resulting from the real time comparisons of metered fuel flow rates at the fuel tank with metered fuel flow rates at the dosing feeder are used for establishing an accurate real time volume-mass law for determination of a fuel flow rate to a helicopter turbine for determining a fuel flow rate.

If the fuel system delivers the data for the mass Mr of the fuel in the fuel tank the improved calculation of the mass Mr of the fuel in the fuel tank by means of the parameters $T_R$ et $V_R$ can be deleted.

Alternatively $b_n$ can be calculated directly according to the following equation:

$$b_n = \frac{a\left[T_m \times \int_{t_{n-1}}^{t_n} Q_m dt - T_R(V_{Rn} - V_{Rn-1})\right]}{(V_{Rn} - V_{Rn-1}) - \int_{t_{n-1}}^{t_n} Q_m dt}$$

with $T_R$ temperature of the fuel tank indicated by the fuel system
Tm temperature of the fuel at the dosing feeder indicated by FADEC
$V_R$ volume of the fuel tanks indicated by metering means of the fuel system corrected according to the aircraft's attitude
Qm Volume flow rate of the fuel at the dosing feeder indicated by FADEC Supplementary to the offset parameter $b_n$, a correction of the inclination parameter a may be done by means of a refined analysis of the evolution of said inclinations as a function of the types of fuels by using a relation:

a=f(permittivity and fuel temperature) indicated by the fuel system.

Facilities for said correction may be implemented in the avionic system.

The invention claimed is:

1. A method of providing a volume-mass law for determination of instant mass fuel flows which are fed by a dosing feeder from a fuel tank to an engine in a helicopter, the method of providing said volume-mass law for determination of fuel flow rates from the fuel tank to said engine, to allow calculation of remaining flight time, point of non-return and fuel quantity left in the fuel tank till landing, including: a step of metering: a permittivity $\xi$ of fuel in the fuel tank, a temperature $T_R$ of fuel in said fuel tank, and a step of determining a sample type of fuel with a given density $\rho_0$ in said fuel tank by associating the measured permittivity $\xi$ and temperature $T_R$ of the fuel in said fuel tank to at least one data pair $\xi$, T of different types of known fuels, said method being characterized by the further steps: said method comprising the steps of:

detecting temperatures Tm and measuring instant volume flow rates $Q_m$ at defined times $t_n$, $t_{n-1}$ ... of the sample type of fuel at said dosing feeder, providing either fuel volumes $V_R$ and temperatures $T_R$ or fuel masses at defined times $t_n$, $t_{n-1}$ ... in said fuel tank, calculating real-time parameters a, b of an equation $\rho = aT + b$ from either fuel volumes and the temperature $T_R$ or fuel masses in said fuel tank, with the parameter $\rho$ for real-time densities $\rho_n$, $\rho_{n-1}$ ... at defined times $t_n$, $t_{n-1}$ ... of a time interval $\Delta t$ from $t_n$ till $t_{n-1}$, the parameter a being a gradient constant and the parameter b being the offset for said given sample fuel, and integrating said instant volume flow rates $Q_m$ during said time interval $\Delta t$ at a value Tm of said temperature, calculated by the mean of said equation for real-time densities $\rho_n$, $\rho_{n-1}$ ... at defined times $t_n$, $t_{n-1}$ ... for providing the volume-mass law.

2. The method according to claim 1, further comprising:

determining a start density $\rho_o$ of said parameter $\rho$ using said equation $\rho_0 = aT + b_0$, with a and $b_0$ being known for said sample type of fuel, providing a fuel mass difference $\Delta M_{Rn}$ at a time $t_n$, from respective masses $M_{Rn}$, $M_{Rn-1}$ of fuel at times $t_n$, $t_{n-1}$ ..., in said fuel tank, calculating a medium value of said temperature $T_R$ during the time interval $\Delta t$, in the fuel tank, measuring said instant volume flow rates $Q_m$ across said dosing feeder at time $t_n$, measuring the temperature Tm at said dosing feeder, integrating the instant volume flow rates $Q_m$ during the time interval $\Delta t$, to a consumed volume Vm of fuel by said engine in said time interval $\Delta t$;

calculating a medium value Tm of said temperature at said dosing feeder, during the time interval $\Delta t$, calculating a dosing meter mass $\Delta Mm_n$ from the consumed volume Vm, by using said equation $\rho = aT + b_n$, with a parameter $b_n$ being a new offset at said defined time $t_n$;

balancing a fuel tank mass $\Delta M_{Rn}$ with the dosing meter mass $Mm_n$, providing a correction factor $K_x$, and calculating a new offset $b_n = K_x \times b_{n-1}$, with a parameter $b_{n-1}$ being a new offset at said defined time $t_{n-1}$, if the balance of the fuel tank mass $\Delta M_{Rn}$ with the dosing meter mass $\Delta Mm_n$ is different from 0, applying said new offset parameter $b_n$ to the equation $\rho = aT + b_n$ before the next respective calculation of fuel tank mass Mr and the dosing meter mass Mm, by using the equation $\rho = aT + b_n$, and repeating x times the above steps from providing said fuel mass difference $\Delta M_{Rn}$ to Applying said new offset parameter $b_n$ to calculate x subsequent offset parameters $b_x$ for subsequent time intervals $\Delta t_x$.

3. The method according to claim 1, further comprising:

determining a start density value $\rho 0$ of said parameter $\rho$ using said equation $\rho_0 = aT + b_0$, with a and $b_0$ being known for said sample type of fuel, measuring a volume $V_{Rn}$ of fuel at a time $t_n$ in said fuel tank, measuring a volume $V_{Rn-1}$ of fuel at a time $t_{n-1}$ in said fuel tank and calculating from said volume $V_{Rn}$ and volume $V_{Rn-1}$ a fuel volume difference $\Delta V_{Rn}$ at a time $t_n$ for the fuel consumed in said fuel tank within a time interval since time $t_{n-1}$ of operation of the engine, calculating a medium value $T_R$ of said temperature during the time interval $\Delta t$ in the fuel tank, measuring an instant volume flow rate $Q_m$ across said dosing feeder at a time $t_n$, measuring the temperature Tm at said dosing feeder, integrating the instant volume flow rate $Q_m$ during the time interval $\Delta t$ of operation, to a consumed volume Vm of fuel by said engine, calculating a medium value Tm of said temperature during the time interval $\Delta t$, calculating a real time new offset parameter $b_n$ for the time $t_n$ from a real time new offset algorithm using the temperature Tm at said dosing feeder, the consumed volume Vm of fuel at said dosing feeder during the time interval $\Delta t$ and the fuel volume difference $\Delta V_{Rn}$ of fuel consumed in said fuel tank during the time interval $\Delta t$, applying said new offset parameter $b_n$ to the equation $\rho = aT + b_{n-1}$ before the respective calculation of fuel density $\rho_n$ at time $t_n$, and repeating x times the above steps from Measuring a volume $V_{Rn}$ of fuel at a time $t_n$ in said fuel tank to Applying said new offset parameter $b_n$ to calculate x subsequent new offset parameters $b_x$ for subsequent time intervals $\Delta t_x$.

4. The method according to claim 3, wherein said real time new offset parameter algorithm is:

$$b_n = \frac{a\left[T_m \times \int_{t_{n-1}}^{t_n} Q_m dt - T_R(V_{Rn} - V_{Rn-1})\right]}{(V_{Rn} - V_{Rn-1}) - \int_{t_{n-1}}^{t_n} Q_m dt}.$$

5. The method according to claim 3, whereby calculating the consumed volume Vm, by integrating the instant volume flow rates Qm during a time interval $\Delta t_n$ of operation of the engine at the medium value Tm of temperature, during the time interval $\Delta t_n$, calculating a fuel tank mass Mr from the consumed volume $V_R$ of fuel in said fuel tank by using said equation, with parameter $\rho_{n-1} = aT + b_{n-1}$, calculating a dosing meter mass Mm from the consumed volume Vm, the equation $\rho_{n-1} = aT + b_{n-1}$, balancing the calculated fuel tank mass Mr with the calculated dosing meter mass Mm, providing a correction factor K and calculating a new offset $b_n = K_n \times b_{n-1}$ if the balance of the fuel tank mass Mr with the dosing meter mass Mm is different from 0, and applying said new offset $b_n$ to the equation $\rho_{n-1} = aT + b_{n-1}$ before the next respective calculation of fuel tank mass Mr and the dosing meter mass Mm, by using the equation $\rho_n = aT + b_n$.

6. The method according to claim 2, for a helicopter having an avionic system metering the temperature Tm of the fuel at said dosing meter, comprising calculating a refined parameter "a" for the equation $\rho_n = aT + b_n$ from an algorithm such as the refined parameter a=f(permittivity and temperature of the fuel) indicated by said avionic system.

7. The method according to claim 2, for a helicopter having display, further comprising displaying as results of the method on said display: determined mass fuel flow rates, remaining flight time, point of non-return and fuel mass quantity left in the fuel tank till landing.

8. The method according to claim 6, further comprising metering with said avionic system, further parameters of the helicopter, e.g. speed, present position, coordinates of the landing.

* * * * *